(12) United States Patent
Yates et al.

(10) Patent No.: US 9,301,683 B2
(45) Date of Patent: Apr. 5, 2016

(54) INTUITIVE TECHNIQUES AND APPARATUS FOR OPHTHALMIC IMAGING

(75) Inventors: Paul Andrew Yates, Charlottesville, VA (US); Kenneth Tran, Burke, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 81 days.

(21) Appl. No.: 13/993,249

(22) PCT Filed: Dec. 13, 2011

(86) PCT No.: PCT/US2011/064558
§ 371 (c)(1),
(2), (4) Date: Sep. 3, 2013

(87) PCT Pub. No.: WO2012/082696
PCT Pub. Date: Jun. 21, 2012

(65) Prior Publication Data
US 2013/0335704 A1    Dec. 19, 2013

Related U.S. Application Data

(60) Provisional application No. 61/422,467, filed on Dec. 13, 2010, provisional application No. 61/524,498, filed on Aug. 17, 2011, provisional application No. 61/524,858, filed on Aug. 18, 2011, provisional application No. 61/568,707, filed on Dec. 9, 2011.

(51) Int. Cl.
*A61B 3/15*   (2006.01)
*A61B 3/14*   (2006.01)

(52) U.S. Cl.
CPC .. *A61B 3/152* (2013.01); *A61B 3/14* (2013.01)

(58) Field of Classification Search
CPC ..... A61B 3/0091; A61B 3/1208; A61B 3/152
See application file for complete search history.

(56) References Cited

U.S. PATENT DOCUMENTS 5,752,100 A    5/1998   Schrock
5,752,115 A    5/1998   McIntyre
(Continued)

FOREIGN PATENT DOCUMENTS

| WO | WO-2010129775 A1 | 5/2010 |
|---|---|---|
| WO | WO-2011029064 A1 | 3/2011 |
| WO | WO-2012082696 A1 | 6/2012 |

OTHER PUBLICATIONS

"International Application Serial No. PCT/US2011/64558, International Search Report mailed Apr. 2, 2012", 2 pgs.
(Continued)

*Primary Examiner* — Jordan Schwartz
(74) *Attorney, Agent, or Firm* — Schwegman Lundberg & Woessner, P.A.

(57) ABSTRACT

Apparatus and techniques can include using one or more of a portable or fixed optical system to obtain images of a desired anatomical target, such as the fundus region of a human eye. The optical system can include one or more of a laser-based focusing target, a laser-based fixation target, or a removable or adjustable alignment assembly. Such an alignment assembly can provide or allow user alignment based on using anatomical landmarks other than the fundus being imaged. One or more of the apparatus or techniques can be implemented in an optical assembly included as a portion hand-held fundus camera, such as including or using a consumer or commercial digital camera to capture an image.

22 Claims, 5 Drawing Sheets

(56) References Cited

U.S. PATENT DOCUMENTS

| | | | |
|---|---|---|---|
| 6,677,565 B1 | 1/2004 | Wahl et al. | |
| 2002/0091323 A1* | 7/2002 | Dreher | 600/476 |
| 2003/0071969 A1 | 4/2003 | Levine et al. | |
| 2005/0157259 A1 | 7/2005 | Akita et al. | |
| 2005/0254008 A1 | 11/2005 | Ferguson et al. | |
| 2007/0002276 A1 | 1/2007 | Hirohara et al. | |
| 2007/0013867 A1* | 1/2007 | Ichikawa | 351/208 |
| 2009/0153797 A1* | 6/2009 | Allon et al. | 351/206 |
| 2010/0056928 A1 | 3/2010 | Zuzak et al. | |

OTHER PUBLICATIONS

"International Application Serial No. PCT/US2011/64558, Written Opinion mailed Apr. 2, 2012", 7 pgs.

"International Application Serial No. PCT/US2011/064558, International Preliminary Report on Patentability mailed Jun. 27, 2013", 9 pgs.

Kerr, Douglas A., "Principle of the Split Image Focusing Aid and the Phase Comparison Autofocus Detector in Single Lens Reflex Cameras", Issue 5, (Aug. 27, 2005), 17 pgs.

* cited by examiner

INTUITIVE TECHNIQUES AND APPARATUS FOR OPHTHALMIC IMAGING

CLAIM OF PRIORITY

This application is a U.S. National Stage Filing under 35 U.S.C. 371 from International Patent Application Serial No. PCT/US2011/064558, filed on Dec. 13, 2011, and published on Jun. 21, 2012 as WO 2012/082696 A1, which claims the benefit of priority to each of the following U.S. Provisional Patent Applications, and each of which is hereby respectively incorporated by reference herein in its respective entirety:

Ser. No. 61/422,467 filed Dec. 13, 2010 and titled "Laser-Based Auto-Focus System for Fundus Photography and Related Methods";

Ser. No. 61/524,498 filed Aug. 17, 2011 and titled "Alignment and Targeting Method for Ophthalmic Imaging";

Ser. No. 61/524,858 filed Aug. 18, 2011 and titled "Laser-based Internal Fixation Targeting Method for Ocular or Ophthalmic Use"; and Ser. No. 61/568,707 filed Dec. 9, 2011 and titled "Intuitive Techniques and Apparatus for Ophthalmic Imaging."

BACKGROUND

The human eye includes a fundus region. Diagnosis and monitoring of various pathologies or diseases can benefit from high-quality imaging of the fundus region. The first commercial fundus cameras were marketed over four decades ago and for the first time allowed clinicians to record retinal pathology on high-quality, photographic film. Fundus photography has since become a useful tool for ophthalmologists to accurately detect, diagnose and treat retinal disease. Since its introduction, fundus camera technology has grown significantly to accommodate the needs of its end-users, namely ophthalmologists and trained ophthalmic photographers.

Although commercially-available fundus cameras have advanced significantly since their introduction, fundus camera design and operation has largely remained unchanged. These cameras are often mounted on a table and are permanent fixtures, requiring patients to sit down and rest their head on a chin rest to obtain static images of the fundus. Further, commercially-available fundus cameras generally require trained ophthalmic technicians to produce correctly composed, focused, and exposed images of the retina. While portable hand-held cameras have been commercially produced, many have failed to gain traction within the ophthalmic community due to various deficiencies such as high cost, difficulty in operation such as involving alignment or focusing issues, or otherwise providing sub-standard image quality.

OVERVIEW

Within the past decade, there has been a growing need for at least semi-automated fundus photography, such as to meet the need for eye screening of a growing population of people at risk for developing potentially blinding eye diseases. Diabetic retinopathy, age-related macular degeneration, and glaucoma are prime clinical examples. Attempts have been made to establish eye screening programs, however they have been severely hampered by factors such as retinal camera cost and difficulty of use. For example, when a fundus camera is placed in the hands of a non-skilled user, over half of acquired fundus images may be misaligned, over or under exposed, or improperly focused. Thus, the present inventors have recognized, among other things, a need for a broad retinal screening platform such as including a low-cost fundus camera that can be used by medical personnel without ophthalmic expertise.

In an example, apparatus and techniques can include using one or more of a portable or fixed optical system to obtain images of a desired anatomical target, such as the fundus region of a human eye. The optical system can include one or more of a laser-based focusing target, a laser-based fixation target, or a removable or adjustable alignment assembly. Such an alignment assembly can provide or allow user alignment based on using anatomical landmarks other than the fundus being imaged. One or more of the apparatus or techniques can be implemented in an optical assembly included as a portion hand-held fundus camera, such as including or using a consumer or commercial digital camera to capture an image.

In an example, an optical apparatus can include an optical lens system that can be configured to relay an image of an anatomical target to an image acquisition assembly via an optical imaging path provided by the optical lens system. For example, the optical lens system can include an objective lens configured to be located near the anatomical target, and an alignment assembly configured to be user-positionable at least partially in the optical imaging path. The optical lens system can include a laser module configured to generate a collimated beam, a diffractive element configured to receive the collimated beam and, in response, to provide a modified beam comprising a focusing target, and a beam splitter located along the optical imaging path, the beam splitter configured to direct at least a portion of the of the modified beam comprising the focusing target to the anatomical target via at least a portion of the optical imaging path including the objective lens.

In an example, an image can be presented to a user via the optical imaging path, such as including a first field of view when the alignment assembly is included at least partially in the optical imaging path, and a second field of view when the alignment assembly is substantially excluded from the optical imaging path. For example, the alignment assembly can be configured to provide an alignment target visible to the user, via the optical imaging path, using the first field of view.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
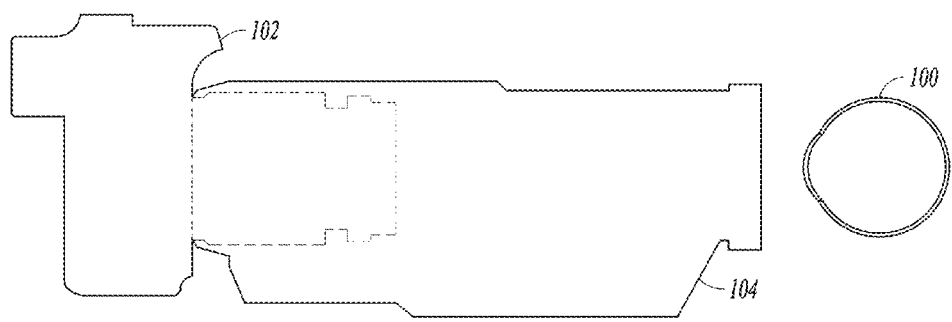
FIG. 1 illustrates generally an apparatus that can include a camera assembly, such as a commercially-available consumer digital or film camera, and an optical assembly that can be attached to the camera assembly.

FIG. 1 illustrates generally an apparatus 100 that can include a camera assembly 102, such as a commercially-available consumer digital or film camera, and an optical assembly 104 that can be attached to the camera assembly.

Various examples of a hand-held fundus camera are included in PCT Application No. PCT/US2010/047909 filed Sep. 3, 2010, which application is hereby incorporated herein by reference in its entirety, including its examples comprising a camera, such as a hand-held camera, including an optical assembly coupled to the camera assembly.

In an example, the optical assembly 104 can be user-attached or detached from the camera assembly 102. Such attachment or detachment can include coupling the optical assembly 104 to an existing lens assembly of the camera assembly 102, or mechanically coupling the optical assembly 104 to one or more of a lens mount, a flash unit mount, a tripod mount, or using one or more other mechanical couplings.

A combination of the optical assembly 104 and the camera assembly 102 can be hand-held. For example, the optical assembly 104 can include portions of one or more of the examples such as shown in FIGS. 2-4, or FIG. 7, or as described in one or more other examples. In an example, such an optical assembly 104 can include one or more illumination sources such as for image composition or image acquisition (e.g., an incandescent source, or a high-intensity flash source such as a xenon flash). In an example, illumination for an image acquisition can be coupled into the optical assembly 104 from a separate housing including a flash unit. Such a flash unit can include a generally-available commercial flash unit, or a custom flash unit.

Figure 2:
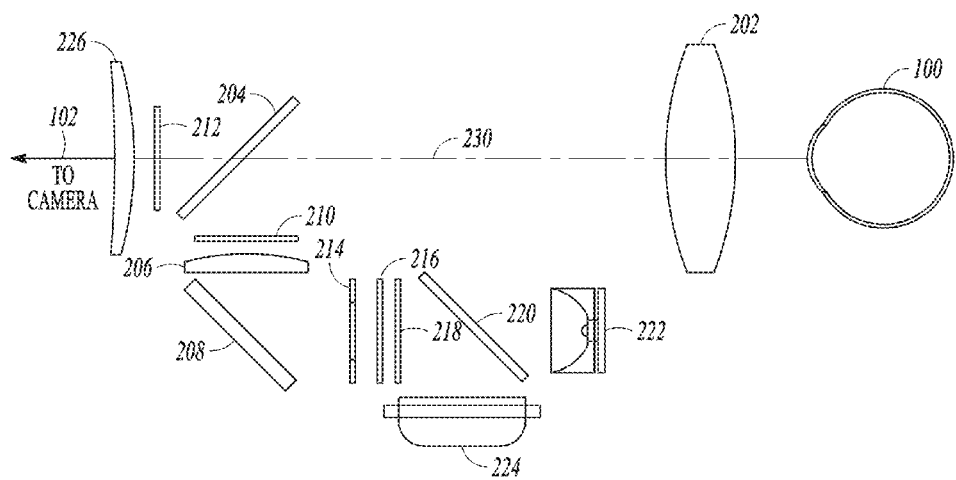
FIG. 2 illustrates generally an apparatus that can be included as a portion of an optical assembly, such as included as a portion of a camera apparatus, or as an optical assembly for use with a camera.

FIG. 2 illustrates generally an apparatus 200 (e.g., an optical lens system) that can be included as a portion of an optical assembly, such as included as a portion of a unitized camera apparatus, or as an optical assembly for use with a camera.

In an example, a fundus camera can include two illumination sources such as a composing illumination source 222 (e.g., an LED or a halogen-based source), and an image acquisition illumination source 224 (e.g., a xenon flash or other source, or including an optical coupling to a more remotely-located source). Illumination from these sources can be directed coaxially to a central illumination pathway (e.g., an optical imaging path 230), such as by using a beam splitter 220. The term "beam splitter" can generically refer to one or more of a mirror, prism, or other structure that can combine or separate incident optical energy. In an example, such a beam splitter 220 can include a hot mirror or a cold mirror, or one or more other types of optical structures that can be used to provide a commonly-shared optical path for the two illumination sources. The composing illumination source 222 can provide illumination including one or more of a visible spectrum or an infrared spectrum.

In an example, illumination can be projected onto an image mask 214 that can be coupled with a diffuser 216, or one or more other filters such as an ultraviolet filter 218, such as converting lambertian light rays into an annular illumination pattern, or into one or more other desired illumination patterns. In an example, illumination light rays can pass through a linear polarizer 210, such as before or after being redirected by a 45° mirror (e.g., a beam splitter 208), such as passing through one or more of a collimating lens 206 (e.g., a converging lens), or a beam splitter 204. Such illumination can then be projected through a front objective lens 202, such as to provide composition illumination or illumination of an anatomical target during image acquisition, such as a portion of a human eye 100.

In an example, an illuminated fundus image, can be passed from the front objective lens 202, back through the beam splitter 204, and through a second linear polarizer 212 (e.g., an "analyzing polarizer). The second linear polarizer 212 can be oriented perpendicular to a polarization sensed by the image sensor, such as to suppress unwanted reflections in an acquired image, such as obtained via a macro lens 226.

Focusing and Alignment Examples

A fundus camera (e.g., an apparatus 100 such as including a camera 102 and an optical assembly 104) can incorporate techniques for automatic image composition or focus abilities. Such capabilities can reduce the training time and expertise necessary for ophthalmic technicians to obtain quality retinal photos.

One approach can include projecting a pair of focusing marks within the optical system. One of such marks can be projected onto the fundus surface and reflected back toward a user. The second mark can be projected such that it lays directly in-line with the focal plane of an imaging sensor. Various techniques can then be used such as to determine where these two focusing marks are in-line with each other, signaling perfect focus, in a manner similar to a prismatic focusing system used in generally-available 35 millimeter single-lens-reflex (SLR) camera systems.

Such an approach, while effective, generally involves complex manufacturing processes due to the need for precise placement of a series of optical mirrors and prisms. This translates into a fundus camera system having a high cost and consuming a large amount of space or volume.

In another approach, a low cost, portable fundus camera can include using generally-available consumer digital camera technology. Leveraging consumer technology can reduce the cost and complexity of the apparatus needed to compose, acquire, and store an image of the fundus. Such a camera may have a built-in auto-focus capability, but such an auto-focus feature, without modification, can be incompatible with prismatic focusing techniques discussed above.

The built-in autofocus technology in consumer cameras can be generally based on two predominant methods: a contrast-based technique or a phase-detection-based technique. Both techniques can use a digital sensor to find a point of focus. Contrast-based techniques are predominantly used in lower-end point-and-shoot cameras. For example, a contrast-based technique can use information about an image projected onto the main imaging sensor of the camera (CCD or CMOS) in order to find the focal point of highest contrast between adjacent pixels. Under varying focal adjustment conditions, the image with the highest contrast in a specified region can be considered the most "in focus."

Phase-detection techniques are generally used for autofocus in higher-end digital SLR cameras. A phase-detection technique can include diverting a portion of the fundus image into two separate images using an optical prism. The images in the image pair can then be compared to each another to find relative differences in phase (e.g. peaks or valleys) such as to determine whether the image is front or back focused. In either case, contrast-based or phase-detection-based techniques generally rely on a fundus image that has clearly defined retinal details in order for the camera to autofocus.

In an example, when imaging mydriatically, a consumer camera sensor can automatically focus on the retinal details inherent in the fundus image. Most commonly, these details could include one or more of the optic nerve or retinal vasculature. While a normal fundus has sufficient contrast to allow for either contrasted-based or phase-detect autofocus, a significant amount of light must be introduced into the eye to allow for the digital sensors to function properly. These increased light levels, while generally not presenting ocular hazard, significantly reduce patient comfort.

Another concern with ophthalmic imaging relates to the ease-of-use of obtaining the correct horizontal, vertical, and depth alignment between a front objective lens of the fundus camera and the subject's eye. Generally, the default viewing angle of the fundus camera is "zoomed-in," such that without prior technical training the camera user is unsure where the camera is located with respect to the external features of the subject's eye.

As such, novice users tend to misinterpret the depth position of the front of the camera, which can increase the difficulty of obtaining a properly composed photograph of the eye fundus. This problem can be compounded when a portable hand-held eye fundus camera is used, since such a hand-held camera generally lacks the stabilization of a tabletop camera, making alignment even more difficult.

Generally, it is clinically important to obtain proper anatomical alignment with the subject's fundus such as to obtain an optic-nerve-centered or macula-centered image. Tabletop fundus cameras generally include internal fixation or external fixation, or both, such as to provide a target on which the subject being imaged can focus or track. However, the simplified design of portable fundus systems generally omit or provide only limited fixation features. Without an internal fixation target, users of portable camera systems must cope with significant eye drift, resulting in out-of-focus or misaligned fundus photographs.

The usability of this auto-focus method further deteriorates during non-mydriatic imaging. In one approach, non-mydriatic imaging can generally include illuminating the fundus with infrared wavelength light to focus and compose the image. Infrared light is used because it does not cause pupillary constriction. Such an infrared technique can introduce at least two problems. The first problem is that infrared light significantly reduces the contrast between retinal vasculature and choroid typically observable in visible-wavelength images. The second problem arises due to the single-sensor design of generally-available consumer cameras.

Even if the camera is able to obtain auto-focus of the infrared illuminated image, the final visible-wavelength image that is acquired will be out-of-focus due to differences in focal length between visible and infrared light waves. The illustrative examples of FIGS. 6A through 6D illustrate generally a difference in obtained focus when using infrared illumination for composition as compared to using a laser-based focusing target as shown in the examples below.

The present inventors have recognized, among other things, that focusing or alignment issues can be addressed such as using an automated or semi-automated technique through which eye fundus photography can be made easier and more novice-friendly. Such techniques can include one or more of 1) user alignment of the fundus camera with the aid of a wide-angle alignment lens and an iris-scleral border target; 2) subject alignment of eye with the fundus camera using an internal fixation target; or 3) automatic laser-based camera focusing of the fundus image.

For example, once the camera is properly positioned, such as using one or more criteria as described in 1) or 2) above, a single-button press by the user can trigger an automated sequence in which the alignment lens is moved out of an optical imaging path, a laser is projected onto the fundus, and the camera locks focus with a projected laser focusing target and captures the final fundus image. A user can obtain mydriatic or non-mydriatic photos of an eye fundus using such techniques.

Figure 3:
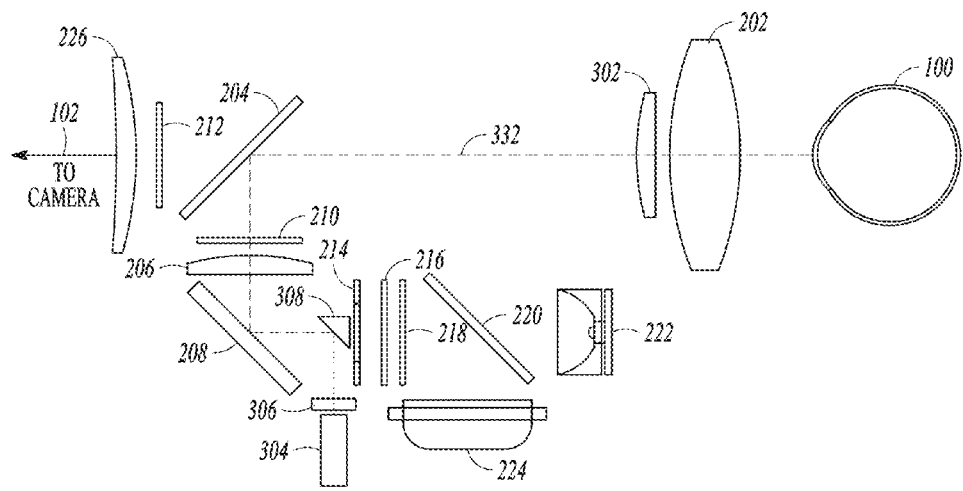
FIG. 3 illustrates generally an apparatus that can include a laser, such as for providing a focusing target, such as included as a portion of a camera apparatus, or as an optical assembly for use with a camera.

FIG. 3 illustrates generally an apparatus 300 (e.g., optical lens system) that can include a laser module 304, such as for providing a focusing target. The apparatus 300 can be included as a portion of a camera apparatus, or as an optical assembly for use with a camera.

In an example, a wide-angle alignment and targeting system can be provided within an ocular fundus imaging system. For example, an alignment assembly can include a convex lens 302 such as with a separate overlay target that can be matched to, or otherwise aligned with, an iris-scleral border of a subject's eye 100. The alignment assembly (e.g., including the convex lens 302) can be mechanically moved into and out of the field of view. For example, the alignment assembly can provide a first field of view comprising a zoomed out view of the subject's external eye (e.g. pupil, iris, sclera). Such a few can allow a user to align a camera including the apparatus 300 such as to fill a circular target with the subject's iris, such as a target 502 as shown in the example of FIG. 5, below.

In an example, the alignment assembly (e.g., including the convex lens 302) can be moved out of the field of view, such as to provide a second field of view comprising a properly composed image of the subject's retina (or another desired target).

In an example, an alignment target can be annular in nature and may be displayed on the viewing screen of the camera. The outside diameter of the target overlay can correspond to a diameter of the outline of an iris-scleral border of the subject to be imaged. This diameter can be specified such that when the convex lens 302 is in place and the user lines up the subject's iris-scleral border to the target, the camera will be positioned in one or more of a desired horizontal, vertical, or depth alignment. For example, when the edge of the subject's iris fills the alignment target, such as overlaying or adjacent to an image of anatomical landmark, then the camera can be properly aligned, after which the lens 302 can be moved out of position and the fundus photograph captured. The alignment target can include a grid, a circle, or one or more other shapes or features.

The present inventors have recognized, among other things, that such an alignment technique can allow the camera user to use a commonly understood anatomical landmark, such as the iris, to properly compose a fundus photograph rather than having to understand the anatomy of the retina. Such apparatus or techniques allow users of a fundus camera to easily align a subject's eye, such as particularly applying to a portable (e.g., hand-held) fundus camera.

In an example, a single-beam or a multiple-beam laser system can be included in an imaging system. The laser system can project fixed-point light sources onto a target region, such as at the back of the subject's eye. Such a light source can be used for positioning the eye fundus, such as focused on by the subject regardless of the subject's ocular refraction. If such a fixation target is provided via a portion of the optical path including the imaging apparatus (e.g., "internal fixation"), the subject's eye fundus can be maintained in proper alignment with the fundus camera, facilitating the acquisition of a clinically appropriate photograph.

In an example, such a fixation target need not include a point. For example, one or more of a holographic or diffraction-based filter 306, such as a diffraction grating, can be used to provide a cross-hair or grid-like image onto the target, such as providing the subject with multiple or varied objects on which to fix.

The present inventors have also recognized that a laser-based fixation technique can be compatible with the optical apparatus including a removable alignment lens optic as described above. For example, a laser is generally focused on the surface to which it is projected, so one or more lenses or other optical structures (e.g., the convex lens 302) can be flipped into or out of the optical pathway without adverse effect on laser image formation. Such flexibility is not present when using generally-available non-coherent light-emitting-diode (LED) fixation techniques or apparatus. In an example, a laser-based fixation technique or apparatus can be included as portion of a low-cost fundus camera based on consumer digital camera technology.

In an example, automatic focus of the retina, or another desired structure, can be obtained during clinical mydriatic and non-mydriatic photography. In an illustrative example, a fixed-focus laser module 304 in the far-red wavelength spectrum can be projected through the holographic or diffraction-based filter 306.

For example, the laser module 304 can provide a coherent beam, such as received by the diffraction-based filter 306, such as to provide a modified beam 332 that can be combined, such as via a beam splitter 308, with light from one or more illumination sources (such as the composing illumination source 222, or the image acquisition illumination source 224). The modified beam 332 can be relayed to the subject's eye 100 such as via a portion of the optical imaging path, such as via one or more of a collimating lens 206 (e.g., a converging lens), a polarizer 210, a beam splitter 204, or an objective lens 202, similar to the corresponding portions shown and discussed in relation to FIG. 2.

For example, laser can be projected onto the retina, providing the camera with a clearly defined target, such as reflected from the subject's eye 100 fundus, and relayed back to the image acquisition assembly such as via one or more of the objective lens 202, the beam splitter 204 (e.g., a partially reflective mirror or prism), an analyzing polarizer 212, or a macro lens 226.

Because the laser can be in the visible range of wavelengths, a focus obtained by the camera can be accurate even under infrared illumination as is generally used for non-mydriatic photography. Also, a visible wavelength laser can be balanced using modulation of power or pulse duration, such as to reduce pupillary constriction. If used in combination with one or more of the alignment examples discussed above or below, the laser may be pulsed on instantaneously such as when the alignment lens is removed from view, enabling the camera to lock focus. As with the example discussed above and below, such a laser-based focusing technique or apparatus can be included as portion of a low-cost fundus camera based on consumer digital camera technology.

In an example, an alignment assembly, such as including the converging lens 302, can be used to align the eye fundus with an optical axis of a fundus camera in one or more of the horizontal, vertical, or depth axes. For example, the alignment assembly can include an optical power in the 10-20 diopter (D) range, or another range. This alignment assembly can provide a "zoomed out" view of the human eye, such as showing major landmarks such as one or more of a brow, an eye lid, a sclera region, or an iris-scleral border. Such anatomical landmarks cannot be visualized within the field of view of a generally-available fundus camera when the camera is placed at the distance generally used to image the eye fundus (e.g., a field-of-view at such a distance generally prevents visualization of such anatomical landmarks in generally-available hand-held fundus cameras).

The alignment assembly can include a lens, such as the converging lens 302, mounted within a lens mount, such as allowing the alignment assembly to move into or out of view of the image acquisition assembly such as via a mechanical positioning apparatus. Such movement of said lens 302 and lens mount can be co-planar or perpendicular with the optical axis 230 of the front objective lens 202. For example, the movement of the lens can be automatically or manually linked to the action of capturing the fundus image, such that before the final image is captured the lens 302 can be moved out of the field of view.

In an example, the alignment assembly can be located between the front objective lens 202 and the imaging device (e.g., an image acquisition assembly such as the camera 102). In an example, the optical axis of the alignment lens can be aligned with the optical axis of one or more of the front objective lens, beam splitter, analyzing polarizer, or image acquisition assembly.

In an example, an alignment target, such as an overlay, can be displayed on a fundus camera 102 display screen (e.g., a liquid crystal display (LCD) or other display). Such a target, in an example, can be circular, such as including a diameter or other feature that corresponds to the subject's iris-scleral border edge.

In an illustrative example, the user of the fundus camera can fill the alignment target with the subject's pupil, such that the iris edge exists coaxial and circumferential with the alignment target. At the depth to which this criterion is achieved, the alignment lens can then be flipped out of view and a desired horizontal, vertical, and depth aligned image of the fundus can be captured. In an example, the alignment target can include one or more of the following: a full or partial annular ring, a quadrant-spaced ring, or including one or more other shapes or features.

Illumination can be provided to the alignment assembly (e.g., including the converging lens 302), the front objective lens 202, or eye fundus using a variety of techniques. For example, before final image capture by the fundus camera, a preview composing illumination source can be used to image the retina for composition purposes. Such an illumination source can travel through a beam splitter 220 and through an image mask 214, such as to produce an annulus of light. This annulus of light can be redirected by the beam splitter 208, such as focused via the collimating lens 206, becoming incident with polarizer 210 (e.g., a pre-polarizer filter).

In an example, the polarizer 210 can polarize the annulus of light to provide a specified polarization axis, which can then be used to reduce internal reflections within the optical system. The annulus of light can be redirected by the beam splitter 204, and can travel to the front objective lens 202. If the converging lens 302 is in place, the light can be incident on the converging lens 302 before being incident on the front objective lens.

Once this light is directed toward the eye 100 fundus, it can then travel back through one or more of the front objective lens 202, the beam splitter 204, or the analyzing polarizer 212. The analyzing polarizer 212 can be configured with its polarization axis oriented perpendicular to the pre-polarizer, such as for suppressing reflections prior to capture by the image acquisition assembly. The polarizing filters can be used to reduce or eliminate internal reflections from the lens surfaces (e.g., reducing or eliminating reflections from one or more glass surfaces).

Fixation Examples

Figure 4:
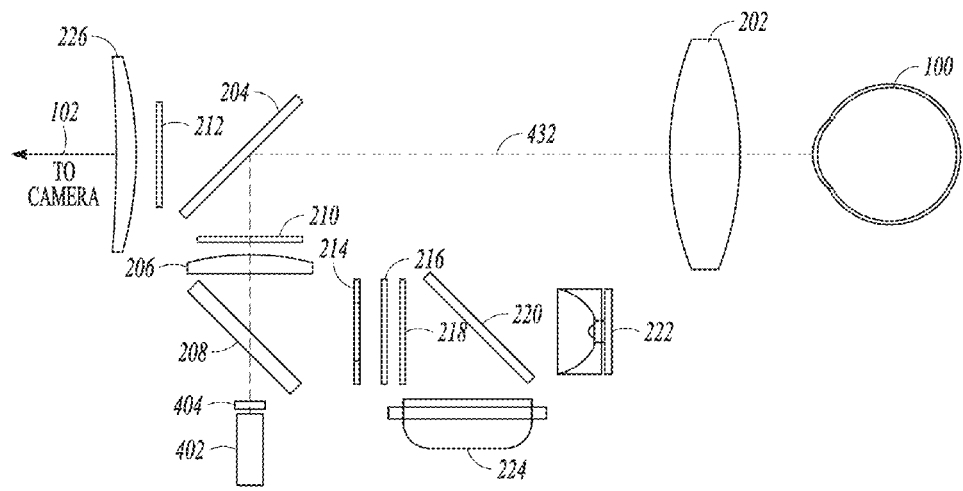
FIG. 4 illustrates generally an apparatus that can include a laser, such as for providing a fixation target to assist a subject in aligning the subject's eye for imaging.

FIG. 4 illustrates generally an apparatus 400 that can include a laser module 402, such as for providing a fixation target to assist a subject in aligning the subject's eye 100 for imaging.

In an example, a single or multi-point laser module 402 and the electronic circuitry to control the laser can be included in a fundus imaging apparatus. The laser module 402 can be integrated into an existing ocular imaging optical system such as occupying a volume of about 1 cubic inch or less, although in some examples, such a laser module can exceed such dimensions. In an example, an external housing can enclose both the optical system components described in one or more of the examples above (e.g., as shown in FIGS. 2-3 or discussed above or below) in addition to the laser module 402.

In an example, the laser module 402 can include a laser that projects a fixed focal point laser beam at or near the center of the optical axis of the ocular imaging system. A lever or other mechanical manipulator can be provided, such as to provide user control over the location of the single-point laser (e.g., in one or two dimensions). In an example, whether by hand or through electronics, or automatic control, the user can position the fixation target generated by the laser onto any point of the imaging subject's retinal field.

In an example, the laser module can include multiple lasers that project multiple fixation targets onto the subject's retina. Such lasers can include different colors, such as within the visible spectrum (e.g., including one or more of green, red or blue), such as to allow the subject being imaged to easily differentiate between separate fixation targets. The multi-point laser module can be controlled electronically through the use of a digital interface or manually by push buttons. In an example, a multiple or varied fixation target can be generated at least in part using a holographic technique or diffraction-grating based filter(s) 404, such as shown and discussed in relation to the examples including a laser-based focusing target. In an example, the laser module 402 can include a class I laser such as including a wavelength included in a range of about 600-700 nanometers (e.g., perceived as a red hue). In an example, such as including multiple lasers, a class I laser can be included such as having a wavelength in a range of about 400-450 nanometers (e.g., a blue hue), or a class I laser having a wavelength in a range of about 500-550 nanometer (e.g., a green hue), in addition to the red laser, or instead of the red laser, or another laser wavelength can be used.

In an example, the polarization axis of the laser beam 332 can established to be different than the polarization axis of a polarizer 210 (e.g., a pre-polarizer) such as to avoid optically blocking the emission from the laser module 402. The polarization axis of the laser beam 332 can include any other polarization angle, such as to allow the subject to see the fixation target, but to also suppress pupil constriction. In an example, a neutral density filter can be used, such as to dim the laser, avoiding pupil constriction or increasing subject comfort. Other techniques can be used to avoid pupil constriction. For example, far-red wavelength lasers in the 650-700 nm range can be used, or modulation of laser intensity can be used (e.g., pulse-width modulation, or one or more other techniques).

The projected laser and formation of a fixed-focal point fixation target can include: providing a laser beam by the laser module, and passing the beam through a neutral density filter. The neutral density filter can block a certain percentage of the optical power output of the laser. In an example, such a neutral density filter can have an optical density value of about 2 and a size of about 5 millimeters square. In an example, a 90%/9% reflectance/transmittance beam splitter 208 can be used to couple a fixation laser beam 332 into the optical imaging path of the apparatus 400.

In an example, the beam 332 can be projected through a collimating lens 206 (e.g., a converging lens), which can shift the optical axis of the laser, and then the beam 332 can pass through the polarizer 210. After the polarizer 210, the laser beam 332 can be reflected off of a second beam splitter 204, such as to direct the laser beam 332 through the front objective lens 202 of the apparatus 400, such as forming an in-focus point of light onto the eye fundus surface. Such an in-focus point of light (or other shape) can provide a fixation target to allow the subject to orient their eye with respect to the ocular imaging camera. Such a laser fixation technique can be compatible with the alignment lens system (e.g., as shown in the example of FIG. 3, such as including a user-positioning alignment assembly comprising the converging lens 302) as described above, such as due to minimal distortion of the laser when passing through the center or near-center of the optical pathway, such as near a central region of one or more lenses.

In an example, the apparatus 400, such as the laser module 402, can be combined with one or more other examples, such as combined with the apparatus shown in FIG. 3. For example, the laser module 402 can be used to provide a fixation target in addition to the focusing target provided by the laser module 304 of the example of FIG. 3. In an example, the laser module 304 of FIG. 3 can be used to provide one or more of a fixation target or a focusing target, instead of, or in addition to, the laser module 402 of the example of FIG. 4. In an example, the laser module 304 of FIG. 3 can include a wavelength that is different from a wavelength specified for the laser module 402, such as for providing one or more fixation targets having a specified perceived color.

One or more of a fixation target wavelength, a duration (e.g., a duty cycle or an overall on-time duration), a fixation target pattern, or an area of the fixation target can be specified such as to reduce or minimize a likelihood of pupillary constriction during alignment or composition in advance of acquiring a fundus image.

Illustrative Examples of Images

Figure 5A:
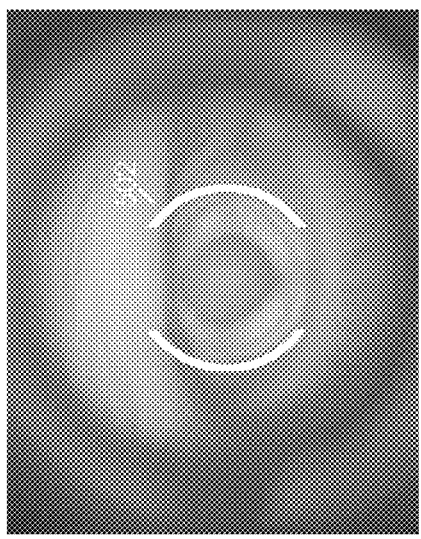
FIGS. 5A through 5C illustrate generally illustrative examples including an alignment overlay in FIG. 5A, a focusing target in FIG. 5B, and a fundus photograph in FIG. 5C, such as obtained via using one or more of the alignment overlay or the focusing target.
Figure 5B:
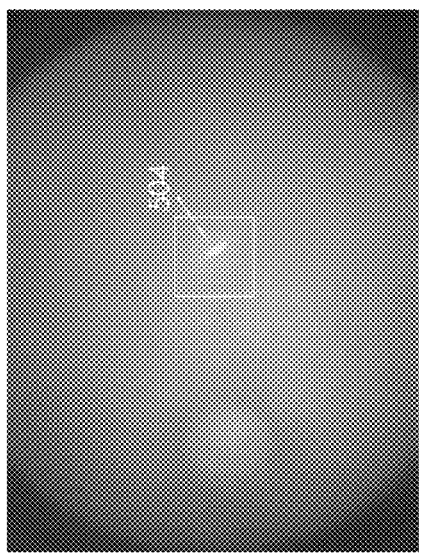
Figure 5C:
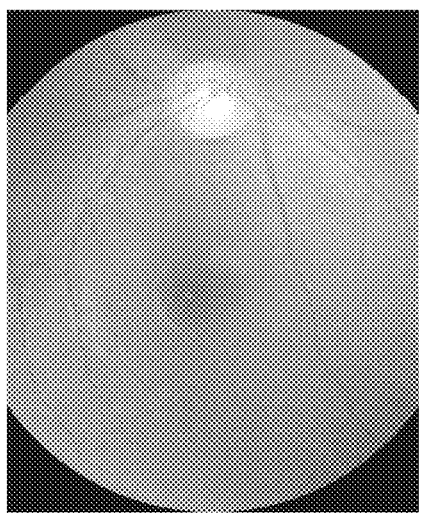

FIGS. 5A through 5C illustrates generally illustrative examples including an alignment target 502 in FIG. 5A, a focusing target 504 in FIG. 5B, and a fundus photograph in FIG. 5C, such as obtained via using one or more of the alignment overlay or the focusing target.

As discussed in the example of FIG. 3, an alignment assembly can be provided, such as including a lens. The alignment assembly can provide a first field of vision for alignment of an optical imaging apparatus (e.g., a hand-held fundus camera) that is different from a second field of vision used for detailed image acquisition of the fundus region. Such an alignment assembly can include a lens, such as a converging lens. In an example, one or more of a software-based alignment target, or an overlay can be provided, such as including the alignment target 502. The imaging apparatus can be positioned, such as by a user, until the alignment target 502 is located over or nearby one or more anatomical landmarks, such as an iris-scleral border as shown in the example of FIG. 5A. The alignment lens can then be substantially removed from an optical imaging path, such as automatically or manually, to provide a second field of vision as shown in FIG. 5B.

Figure 6A:
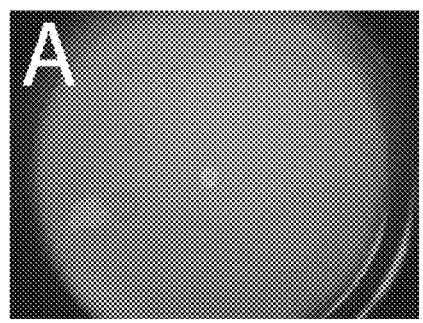
FIGS. 6A through 6D illustrate generally an illustrative example of a comparison between a fundus image obtained using infrared illumination and lacking a laser-based focusing target, as compared to a fundus image obtained using a laser-based focusing target.
Figure 6B:
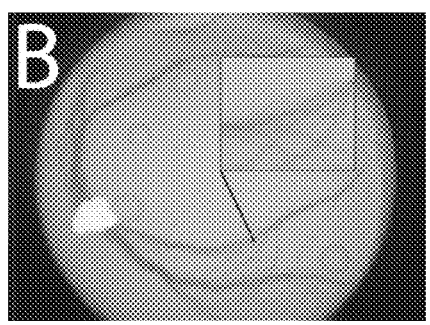
Figure 6C:
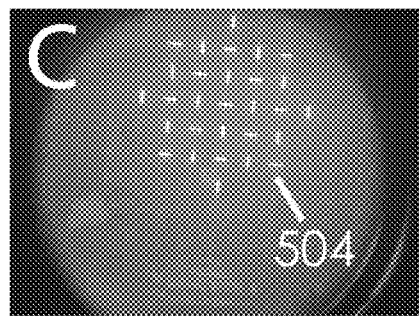

In an example, a laser can be projected onto the human fundus in order to provide a fundus camera with the image contrast to facilitate automatic focus, such as including a focusing target 504 or as shown in FIG. 6C, or including one or more other patterns or arrays of points. In an example, a low-cost fundus camera can include using consumer digital camera technology. For example, laser-based technique as shown in the examples of FIG. 5B or FIG. 6C, and discussed elsewhere above, can be compatible with consumer auto-focusing techniques including contrast-based or phase-detect based autofocus techniques, such as used in point-and-shoot or DSLR cameras, without requiring modification of such cameras.

In an example, the photograph in FIG. 5C can be obtained, such as using am alignment target as shown in FIG. 5A, such as under infrared illumination. An image acquisition apparatus, such as a camera, can then obtain focus on a focusing target 504, such as shown in FIG. 5B, such as using a zoomed-in field of view. The focusing target can then be switched off or otherwise suppressed, such as to obtain the fundus photograph of FIG. 5C.

FIGS. 6A through 6D illustrate generally an illustrative example of a comparison between a fundus image obtained using infrared illumination and lacking a laser-based focusing target, as compared to a fundus image obtained using a laser-based focusing target.

For example, in the illustrative example of FIG. 6A, a model of an eye under 780 nanometer illumination is shown, such as without use of a focusing target other than the anatomy of the model eye. A corresponding visibly-exposed image is shown in the illustrative example of FIG. 6B. The focal planes for a particular configuration of optical lenses can be different, such as depending on the wavelength of illumination. If manual or automatic focusing is performed using infrared illumination for composition, such as shown in FIG. 6A, a corresponding visibly-exposed image can be out-of-focus as shown in FIG. 6B.

In contrast, in an example, a focusing target 504 (e.g., formed holographically such as with a diffractive element) can be projected onto the back of the retina for a brief period of time (e.g., less than about a second, or for another specified duration), such as including enough time for a camera to obtain autofocus. In an example, composing illumination can (either in the visible or IR wavelengths) be turned off during this time. This allows a low power laser pattern to be significantly brighter than the surrounding fundus. The otherwise unlit fundus image (except for the laser pattern) can then be relayed back to the camera sensor via the optics of a fundus camera, producing in image such as shown in FIG. 6C.

In an illustrative example, such as using apparatus as shown in the examples of one or more of FIGS. 3-4, the laser-based focusing target 504 can be provided by a collimated laser beam passed through a diffraction grating such as to produce a distinct laser pattern. One or more of internal or external reflections can be suppressed such as using one or more of a pair of perpendicularly crossed linear polarizers, a perpendicularly placed translating 45° mirror, a collimating lens, a beam splitter, and a front-objective lens of power of about 22D, or using one or more other optical components.

Figure 6D:
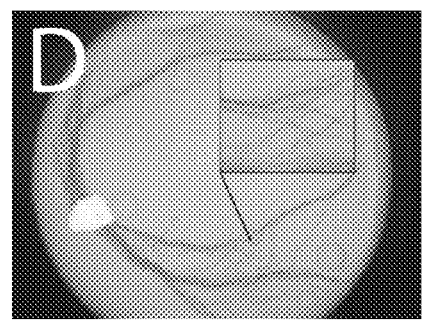

Once the camera obtains focus, the laser pattern can be turned off and an image acquisition illumination source (e.g., a xenon flash) can be used to acquire the final fundus image, such as shown in the illustrative example of FIG. 6D. The images shown in FIG. 6C and 6D can exist at the same focal point due to the collimated nature of the laser projection pattern. Using such a technique, the camera's ability to autofocus is enhanced in a desired focal plane, such as including a fundus region of the eye.

Such a laser-projection system does not require the multiple beam splitters, mirrors, or prisms associated with generally-available prismatic focusing techniques, allowing such a system to be made more compact than a purely-prismatic system. For example, the laser-based system can be included as a subassembly that is attachable to an off-the-shelf camera with minimal or no modification to the off-the-shelf camera.

Due to the nature of the optical system, an element placed within the central optical imaging path can generally interfere with imaging of the fundus. In order to introduce a collimated laser that is coaxial with the central imaging and illumination path, a small relay mirror can be sized to fit within a center circle of the image mask, such as oriented at a 45° angle. In an example, such a relay mirror can be sized to be smaller than about 7 millimeters (mm)×7 mm×10 mm. The laser can then be placed nearby the optical axis of the fundus camera, such as oriented so that the laser projects perpendicularly to the optical axis and is incident on the center of the relay mirror, such as shown in the examples of FIGS. 3-4.

In an example, a holographic laser pattern can be generated by placing a specialized diffraction grating (e.g., a diffractive element) to receive a collimated beam provided by a laser module. For example, such a diffraction grating can produce a laser pattern specified to aid in focusing, such as including a series of cross-hatches, a line, a cross-hair, a grid, or a circle of a series of point source lights, or including one or more other patterns or shapes.

Projecting a laser pattern through the optical system can result in a number of image artifacts. These can result from reflections off the front object lens or the cornea of the subject being imaged. As discussed in the examples above, a polarization-based technique can be used to reduce such reflections. For example, a pair of perpendicularly crossed linear polarizers can be used to reduce or eliminate such reflection. Because lasers generally emit plane-polarized light (p-polarized) at a specific angle, the laser polarization can specified such that the polarization angle is at a 45° angular offset relative to the polarization angle of a first linear polarizer. A second linear polarizer can be oriented at a 90° angular offset relative to the first polarizer.

Thus, reflections off of hard composite surfaces (e.g. glass) maintain their original polarization state and can be blocked by the second polarizer. The laser pattern reflected from the fundus changes polarization state slightly upon contact with the retinal surface. Due to such induced polarization diversity, at least a portion of the reflected laser pattern can then be able to pass through the second polarizer. The configuration of the laser, the first, and the second polarizers can be used to reduce or eliminate front lens reflections while retaining the ability of the camera to image the laser-pattern-lit fundus, such as to lock focus on such a laser pattern.

Use of a reflection suppression technique, such as using one or more polarizers, can decrease or eliminate an inadvertent focus on an intermediate surface such as a lens or mirror surface, during focusing by the user or during an autofocusing attempt by the camera. For example, a specular reflection of the laser focusing target from a lens might appear brighter than an actual desired reflection of the focusing target from the absorbing fundus region, in the absence of suppression of unwanted reflections.

In an example, a laser-based autofocus system can be implemented in a non-mydriatic fundus camera. In such an example, pupillary constriction due to light exposure can be a concern. In order to minimize the probability or degree of pupil constriction, a laser wavelength of 670 nm or higher can be used. The response of the human retina to near-IR wavelengths is significantly less than for light in the 400 to 600 nm range. Unlike the human eye, charge-coupled-device (CCD) or complementary metal-oxide-semiconductor (CMOS) sensors are generally able to image up to the IR range.

For example, an image sensor of a commercially-available digital camera can have its IR-blocking filter removed, thus allowing for the camera to see the laser pattern without any decrease in intensity. This relative difference in observed laser intensity between the human eye and a digital sensor can be exploited to enable use in the non-mydriatic case. Pupillary constriction can further be reduced by controlling the pulse duration of the laser. For example, such a pulse duration can be <400 milliseconds (ms) which can still allow the camera to obtain focus.

The laser system can be a portion of a relatively low-cost fundus camera based on a consumer digital camera. For example, the camera can be focused at visible wavelengths using a visible-wavelength laser focusing target. Such a camera can still be used for non-mydriatic image composition under IR illumination, but with actual image capture using visible light (e.g., a xenon flash). Different image focal planes occurring from composing the image under infrared light and taking the final fundus image using visible light can be eliminated because the focusing is accomplished using visible light.

Examples of Techniques That Can Include Focusing and Alignment Aspects

Use of one or more of the techniques or apparatus outlined in the examples above and below can permit non-mydriatic imaging of the fundus without the need for infrared illumination. For example, the fundus camera can include external low-power LEDs in the visible (e.g., red spectrum) which can illuminate the exterior of the eye (e.g., sclera, eye brow, eye lid). This can provide illumination for the user to align the camera with an overlaid iris-scleral border target. Pupillary constriction can thus be reduced or eliminated because lighting of the exterior anatomy is indirect, as opposed to techniques including direct illumination of the fundus.

A user of a fundus camera can position the subject within range of the front objective lens of an optical imaging apparatus, such as about 5 mm to 10 mm away from the subject to be imaged. In an example, one or more of an eye-cup or a shroud can be included as a portion of the apparatus, such as to provide a rough gauge to position the imaging apparatus relative to the subject.

In an example, a user attempting to position the optical apparatus can "flip" or otherwise position an alignment lens in place and looks at the preview composing screen of the fundus camera (or another display showing an image to assist the user in composing the image). The user can move the fundus camera or the subject in x-y-z planes such as to align the subject's iris-scleral border coaxially and circumferentially with an alignment target.

After alignment, the user can depress the shutter button of the fundus camera, such as triggering the movement of the alignment lens out of the field of view. A focus laser can then be turned on for a brief duration. Once the camera has determined the proper focal plane, a properly aligned and composed image of the eye fundus can be captured. In an example, the subject's eye can fixated on a target provided by an internal fixation laser, which can also assist keeping the camera and eye coaxially aligned.

A microcontroller, microprocessor, or other apparatus can be used to coordinate one or more automated aspects of such an imaging sequence. The user can activate this sequence with the press of a single button. The microcontroller can generally control one or more of timing and pulse duration between removing the alignment lens, turning on the focusing laser, or signaling the camera to focus and acquire the final image.

Figure 7:
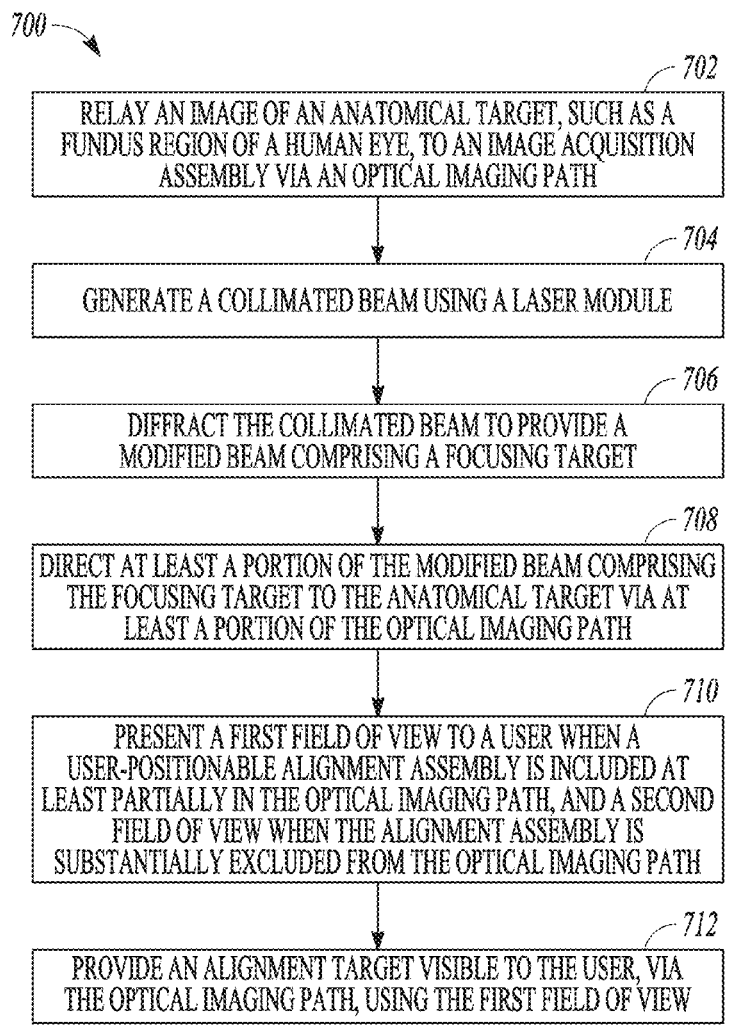
FIG. 7 illustrates generally a technique that can include relaying an image of an anatomical target to an image acquisition assembly via an optical imaging path provided by the optical lens system including an objective lens configured to be located near the anatomical target, and an alignment assembly configured to be user-positionable at least partially in the optical imaging path.

FIG. 7 illustrates generally a technique 700, such as a method, that can include relaying an image of an anatomical target to an image acquisition assembly via an optical imaging path provided by the optical lens system including an objective lens configured to be located near the anatomical target, and an alignment assembly configured to be user-positionable at least partially in the optical imaging path. The technique 700, can include apparatus or techniques such as discussed in the examples above or below, such as using one or portions of the apparatus of FIGS. 1 through 4, FIGS. 5A through 5C, or FIGS. 6A through 6D.

At 702, the technique 700 can include relaying an image of an anatomical target to an image acquisition assembly via an optical imaging path provided by an optical lens system. The optical lens system can include an objective lens configured to be located near the anatomical target, and an alignment assembly configured to be user-positionable at least partially in the optical imaging path.

At 704, the technique 700 can include generating a collimated beam using a laser module. At 706, the collimated beam can be diffracted, such as to provide a modified beam comprising a focusing target. At 708, at least a portion of the modified beam comprising the focusing target can be directed to the anatomical target via at least a portion of the optical imaging path, such as including the objective lens.

At 710, a first field of view can be presented to a user when the alignment assembly is included at least partially in the optical imaging path, and a second field of view can be presented when the alignment assembly is substantially excluded from the optical imaging path. At 712, an alignment target can be provided. In an example, the alignment target can be visible to the user, via the optical imaging path, using the first field of view.

Various Notes & Examples

Example 1 can include subject matter, such as an apparatus, a method, a means for performing acts, or a machine readable medium including instructions that, when performed by the machine, can cause the machine to perform acts), such as can include an optical lens system configured to relay an image of an anatomical target to an image acquisition assembly via an optical imaging path provided by the optical lens system, the optical lens system including an objective lens configured to be located near the anatomical target, and an alignment assembly configured to be user-positionable at least partially in the optical imaging path. Example 1 can include a laser module configured to generate a collimated beam, a diffractive element configured to receive the collimated beam and, in response, to provide a modified beam comprising a focusing target, and a beam splitter located along the optical imaging path, the beam splitter configured to direct at least a portion of the of the modified beam comprising the focusing target to the anatomical target via at least a portion of the optical imaging path including the objective lens.

Example 1 can also include an image presented via the optical imaging path including a first field of view when the alignment assembly is included at least partially in the optical imaging path, and a second field of view when the alignment assembly is substantially excluded from the optical imaging path, and an alignment assembly configured to provide an alignment target visible to the user, via the optical imaging path, using the first field of view.

Example 2 can include, or can optionally be combined with the subject matter of Example 1, to optionally include apparatus for imaging an anatomical target including a fundus region of a human eye, an alignment assembly includes a lens, a first field of view is wider than the second field of view, including a first field of view sufficiently wide to show at least an iris-scleral border, and an optical apparatus configured to be positionable by the user so that the alignment target appears, via the optical imaging path, to be located at or near an anatomical landmark when the optical apparatus is in a desired orientation for acquisition of an image of the fundus region.

Example 3 can include, or can optionally be combined with the subject matter of one or any combination of Examples 1 through 2 to optionally include one or more of an intensity or a pattern of the focusing target is adjusted to provide a fixation target visible to an imaging subject when the fixation target is projected at an eye of the subject.

Example 4 can include, or can optionally be combined with the subject matter of one or any combination of Examples 1 through 3 to optionally include a second laser module configured to generate a second beam, the second beam specified to provide a fixation target visible to an imaging subject when the fixation target is projected toward an eye of the imaging subject.

Example 5 can include, or can optionally be combined with the subject matter of one or any combination of Examples 1 through 4 to optionally include a second beam splitter located along the optical imaging path, the beam splitter configured to direct at least a portion of the of the second beam comprising the fixation target for projection toward the eye of the imaging subject via at least a portion of the optical imaging path including the objective lens.

Example 6 can include, or can optionally be combined with the subject matter of one or any combination of Examples 1 through 5 to optionally include a focusing target including a specified pattern generated using the diffractive element.

Example 7 can include, or can optionally be combined with the subject matter of one or any combination of Examples 1 through 6 to optionally include an optical lens system configured to relay a reflection of the focusing target through the optical lens system to the image acquisition assembly, the reflection provided by the anatomical target.

Example 8 can include, or can optionally be combined with the subject matter of one or any combination of Examples 1 through 7 to optionally include the image acquisition assembly, the image acquisition assembly configured to automatically obtain a focus on a desired portion of the anatomical target using the reflection of the focusing target relayed to the image acquisition assembly via the optical lens system, and a laser module configured to provide a beam including energy in the visible spectrum.

Example 9 can include, or can optionally be combined with the subject matter of one or any combination of Examples 1 through 8 to optionally include one or more of the optical lens system, the laser module, the diffractive element, or the beam splitter included as a portion of an optical assembly configured for one or more of mechanical attachment to the image acquisition assembly or optical coupling to the image acquisition assembly.

Example 10 can include, or can optionally be combined with the subject matter of one or any combination of Examples 1 through 9 to optionally include an image acquisition assembly comprising a digital camera, wherein the optical assembly is mechanically attached to the digital camera, wherein the combination of the digital camera and the optical assembly is sized and shaped to be hand-held, and wherein the combination is configured for acquisition of an image of the anatomical target when hand-held.

Example 11 can include, or can optionally be combined with the subject matter of one or any combination of Examples 1 through 10 to optionally include a digital camera comprising a user input configured to trigger an acquisition of a fundus image, the digital camera configured to automatically obtain a focus on a desired portion of the anatomical target using the reflection of the focusing target relayed to the image acquisition assembly via the optical lens system, and, in response to the user input to trigger an acquisition, the optical apparatus configured to automatically perform at least one of repositioning the alignment assembly, enabling a projection of the focusing target onto the anatomical target for at least a specified duration during which the digital camera obtains focus, or disabling projection of the focusing target after the digital camera obtains focus.

Example 12 can include, or can optionally be combined with the subject matter of one or any combination of Examples 1-11 to include, subject matter (such as an apparatus, a method, a means for performing acts, or a machine readable medium including instructions that, when performed by the machine, that can cause the machine to perform acts), such as can include relaying an image of an anatomical target to an image acquisition assembly via an optical imaging path provided by an optical lens system including an objective lens configured to be located near the anatomical target and an alignment assembly configured to be user-positionable at least partially in the optical imaging path.

Example 12 can also include generating a collimated beam using a laser module, diffracting the collimated beam to provide a modified beam comprising a focusing target, directing at least a portion of the modified beam comprising the focusing target to the anatomical target via at least a portion of the optical imaging path including the objective lens, presenting a first field of view to a user when the alignment assembly is included at least partially in the optical imaging path, and a second field of view when the alignment assembly is substantially excluded from the optical imaging path, and providing an alignment target visible to the user, via the optical imaging path, using the first field of view.

Example 13 can include, or can optionally be combined with the subject matter of Example 12, to optionally include using an anatomical target including a fundus region of a human eye, an alignment assembly includes a lens, a first field of view that is wider than the second field of view, including a first field of view sufficiently wide to show at least an iris-scleral border.

Example 13 can also include positioning the optical apparatus in a desired orientation for acquisition of an image using the alignment target, the alignment target appearing to the user, via the optical imaging path, to be located at or near an anatomical landmark when the optical apparatus is in the desired orientation for acquisition of an image of the fundus region.

Example 14 can include, or can optionally be combined with the subject matter of one or any combination of Examples 12 through 13 to optionally include adjusting an intensity of or a pattern of the focusing target to provide a fixation target visible to an imaging subject when the fixation target is projected at an eye of the subject.

Example 15 can include, or can optionally be combined with the subject matter of one or any combination of Examples 12 through 14 to optionally include generating a second beam specified to provide a fixation target visible to an imaging subject when the target is projected toward an eye of the imaging subject.

Example 16 can include, or can optionally be combined with the subject matter of one or any combination of Examples 12 through 15 to optionally include directing at least a portion of the second beam comprising the fixation target for projection toward the eye of the imaging subject via at least a portion of the optical imaging path including the objective lens.

Example 17 can include, or can optionally be combined with the subject matter of one or any combination of Examples 12 through 16 to optionally include diffracting the collimated beam to provide a modified beam comprising a focusing target including providing a specified pattern using a diffractive element.

Example 18 can include, or can optionally be combined with the subject matter of one or any combination of Examples 12 through 17 to optionally include relaying a reflection of the focusing target through the optical lens system to the image acquisition assembly, the reflection provided by the anatomical target.

Example 19 can include, or can optionally be combined with the subject matter of one or any combination of Examples 12 through 18 to optionally include automatically obtaining a focus on a desired portion of the anatomical target using the reflection of the focusing target relayed to the image acquisition assembly via the optical lens system, the laser module configured to provide a beam including energy in the visible spectrum.

Example 20 can include, or can optionally be combined with the subject matter of one or any combination of Examples 12 through 19 to optionally include using an image acquisition assembly comprising a digital camera, and one or more of the optical lens system, the laser module, the diffractive element, or the beam splitter included as a portion of an optical assembly configured for one or more of mechanical attachment to the image acquisition assembly, or optical coupling to the digital camera.

Example 20 can also include, mechanically attaching the optical assembly to the digital camera, the combination of the digital camera and the optical assembly sized and shaped to be hand-held, and the combination configured for acquisition of an image of the anatomical target when hand-held.

Example 21 can include, or can optionally be combined with the subject matter of one or any combination of Examples 12 through 20 to optionally include automatically obtaining a focus on a desired portion of the anatomical target using the reflection of the focusing target relayed to the image acquisition assembly via the optical lens system, and in response to an input to trigger an acquisition, automatically performing at least one of repositioning the alignment assembly, enabling a projection of the focusing target onto the anatomical target for at least a specified duration during which the digital camera obtains focus, or disabling projection of the focusing target after the digital camera obtains focus.

Example 22 can include, or can optionally be combined with the subject matter of one or any combination of Examples 1-21 to include, subject matter (such as an apparatus, a method, a means for performing acts, or a machine readable medium including instructions that, when performed by the machine, that can cause the machine to perform acts), that can include an optical lens system configured to relay an image of an anatomical target to an image acquisition assembly via an optical imaging path provided by the optical lens system, the optical lens system including an objective lens configured to be located near the anatomical target and an alignment assembly configured to be user-positionable at least partially in the optical imaging path.

Example 22 can also include a laser module configured to generate a collimated beam, a diffractive element configured to receive the collimated beam and, in response, to provide a modified beam comprising a focusing target, and a beam splitter located along the optical imaging path, the beam splitter configured to direct at least a portion of the of the modified beam comprising the focusing target to the anatomical target via at least a portion of the optical imaging path including the objective lens.

Example 22 can also include an image presented via the optical imaging path including a first field of view when the alignment assembly is included at least partially in the optical imaging path, and a second field of view when the alignment assembly is substantially excluded from the optical imaging path, an alignment assembly configured to provide an alignment target visible to the user, via the optical imaging path, using the first field of view, the anatomical target including a fundus region of a human eye, the first field of view wider than the second field of view, including a first field of view sufficiently wide to show at least an iris-scleral border, and the optical apparatus configured to be positionable by the user so that the alignment target appears, via the optical imaging path, to be located at or near an anatomical landmark when the optical apparatus is in a desired orientation for acquisition of an image of the fundus region.

Example 23 can include, or can optionally be combined with any portion or combination of any portions of any one or more of Examples 1-22 to include, subject matter that can include means for performing any one or more of the functions of Examples 1-22, or a machine-readable medium including instructions that, when performed by a machine, cause the machine to perform any one or more of the functions of Examples 1-22.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An optical apparatus, comprising:
   an optical lens system configured to relay an image of an anatomical target to an image acquisition assembly via an optical imaging path provided by the optical lens system, the optical lens system including:
      an objective lens configured to be located near the anatomical target; and
      an alignment assembly configured to be user-positionable at least partially in the optical imaging path;
   a laser module configured to generate a collimated beam;
   a diffractive element configured to receive the collimated beam and, in response, to provide a modified beam comprising a focusing target; and
   a beam splitter located along the optical imaging path, the beam splitter configured to direct at least a portion of the of the modified beam comprising the focusing target to the anatomical target via at least a portion of the optical imaging path including the objective lens;
   wherein an image presented via the optical imaging path includes a first field of view to provide an image of an anatomical landmark when the alignment assembly is included at least partially in the optical imaging path, and a second field of view to provide the image of the anatomical target when the alignment assembly is substantially excluded from the optical imaging path; and
   wherein the focusing target is produced and is presented to the image acquisition assembly without use of a prismatic focusing aid.

2. The optical apparatus of claim 1, wherein:
   the anatomical target includes a fundus region of a human eye;
   the alignment assembly includes a lens;
   the first field of view is wider than the second field of view, including a first field of view sufficiently wide to show at least an iris-scleral border; and
   the optical apparatus is configured to be positionable by the user so that an alignment target appears to be located at or near the anatomical landmark when the optical apparatus is in a desired orientation for acquisition of an image of the fundus region.

3. The optical apparatus of claim 1, wherein one or more of an intensity or a pattern of the focusing target is specified to provide a fixation target visible to an imaging subject when the fixation target is projected at an eye of the subject.

4. The optical apparatus of claim 1, comprising a second laser module configured to generate a second beam, the second beam specified to provide a fixation target visible to an imaging subject when the fixation target is projected toward an eye of the imaging subject.

5. The optical apparatus of claim 4, comprising a second beam splitter located along the optical imaging path, the beam splitter configured to direct at least a portion of the second beam comprising the fixation target for projection toward the eye of the imaging subject via at least a portion of the optical imaging path including the objective lens.

6. The optical apparatus of claim 1, wherein the focusing target includes a specified pattern generated using the diffractive element.

7. The optical apparatus of claim 1, wherein the optical lens system is configured to relay a reflection of the focusing target through the optical lens system to the image acquisition assembly, the reflection provided by the anatomical target.

8. The optical apparatus of claim 7, further comprising the image acquisition assembly, wherein the image acquisition assembly is configured to automatically obtain a focus on a desired portion of the anatomical target using the reflection of the focusing target relayed to the image acquisition assembly via the optical lens system; and
   wherein the laser module is configured to provide a beam including energy in the visible spectrum.

9. The optical apparatus of claim 1, wherein one or more of the optical lens system, the laser module, the diffractive element, or the beam splitter are included as a portion of an optical assembly configured for one or more of mechanical attachment to the image acquisition assembly or optical coupling to the image acquisition assembly.

10. The optical apparatus of claim 9, wherein the image acquisition assembly comprises a digital camera, wherein the optical assembly is mechanically attached to the digital camera, wherein the combination of the digital camera and the optical assembly is sized and shaped to be hand-held, and wherein the combination is configured for acquisition of an image of the anatomical target when hand-held.

11. The optical apparatus of claim 10, wherein the digital camera includes a user input configured to trigger an acquisition of a fundus image;
wherein the digital camera is configured to automatically obtain a focus on a desired portion of the anatomical target using the reflection of the focusing target relayed to the image acquisition assembly via the optical lens system without using a prismatic focusing aid; and
wherein, in response to the user input to trigger an acquisition, the optical apparatus is configured to automatically perform at least one of repositioning the alignment assembly, enabling a projection of the focusing target onto the anatomical target for at least a specified duration during which the digital camera obtains focus, or disabling projection of the focusing target after the digital camera obtains focus.

12. A method, comprising:
relaying an image of an anatomical target to an image acquisition assembly via an optical imaging path provided by an optical lens system including:
an objective lens configured to be located near the anatomical target; and
an alignment assembly configured to be user-positionable at least partially in the optical imaging path;
generating a collimated beam using a laser module;
diffracting the collimated beam to provide a modified beam comprising a focusing target;
directing at least a portion of the modified beam comprising the focusing target to the anatomical target via at least a portion of the optical imaging path including the objective lens;
presenting a first field of view to a user when the alignment assembly is included at least partially in the optical imaging path, the first field of view to provide an image of an anatomical landmark; and
presenting a second field of view when the alignment assembly is substantially excluded from the optical imaging path, the second field of view to provide the image of the anatomical target;
wherein the focusing target is produced and is presented to the image acquisition assembly without use of a prismatic focusing aid.

13. The method of claim 12, wherein the anatomical target includes a fundus region of a human eye;
wherein the alignment assembly includes a lens;
wherein the first field of view is wider than the second field of view, including a first field of view sufficiently wide to show at least an iris-scleral border;
wherein the method includes positioning the optical apparatus in a desired orientation for acquisition of an image so that an alignment target appears to the user to be located at or near the anatomical landmark when the optical apparatus is in the desired orientation for acquisition of an image of the fundus region.

14. The method of claim 12, comprising providing a specified intensity of or a specified pattern of the focusing target to provide a fixation target visible to an imaging subject when the fixation target is projected at an eye of the subject.

15. The method of claim 12, comprising generating a second beam specified to provide a fixation target visible to an imaging subject when the fixation target is projected toward an eye of the imaging subject.

16. The method of claim 15, comprising directing at least a portion of the second beam comprising the fixation target for projection toward the eye of the imaging subject via at least a portion of the optical imaging path including the objective lens.

17. The method of claim 12, wherein the diffracting the collimated beam to provide a modified beam comprising a focusing target includes providing a specified pattern using a diffractive element.

18. The method of claim 12, comprising relaying a reflection of the focusing target through the optical lens system to the image acquisition assembly, the reflection provided by the anatomical target.

19. The method of claim 18, comprising automatically obtaining a focus on a desired portion of the anatomical target using the reflection of the focusing target relayed to the image acquisition assembly via the optical lens system; and
wherein the laser module is configured to provide a beam including energy in the visible spectrum.

20. The method of claim 12, wherein the image acquisition assembly comprises a digital camera;
wherein one or more of the optical lens system, the laser module, the diffractive element, or the beam splitter are included as a portion of an optical assembly that can be one or more of mechanically attached to the digital camera or optically coupled to the digital camera;
wherein the method includes mechanically attaching or optically coupling the optical assembly to the digital camera;
wherein the combination of the digital camera and the optical assembly is sized and shaped to be hand-held; and
wherein the combination is configured for acquisition of an image of the anatomical target when hand-held.

21. The method of claim 20, comprising automatically obtaining a focus on a desired portion of the anatomical target using the reflection of the focusing target relayed to the image acquisition assembly via the optical lens system; and
in response to an input to trigger an acquisition, automatically performing at least one of repositioning the alignment assembly, enabling a projection of the focusing target onto the anatomical target for at least a specified duration during which the digital camera obtains focus, or disabling projection of the focusing target after the digital camera obtains focus.

22. An optical apparatus, comprising:
an optical lens system configured to relay an image of an anatomical target to an image acquisition assembly via an optical imaging path provided by the optical lens system, the optical lens system including:
an objective lens configured to be located near the anatomical target; and
an alignment assembly configured to be user-positionable at least partially in the optical imaging path;
a laser module configured to generate a collimated beam;

a diffractive element configured to receive the collimated beam and, in response, to provide a modified beam comprising a focusing target; and a beam splitter located along the optical imaging path, the beam splitter configured to direct at least a portion of the of the modified beam comprising the focusing target to the anatomical target via at least a portion of the optical imaging path including the objective lens;

wherein an image presented via the optical imaging path includes a first field of view to provide an image of an anatomical landmark when the alignment assembly is included at least partially in the optical imaging path, and a second field of view to provide the image of the anatomical target when the alignment assembly is substantially excluded from the optical imaging path;

wherein the focusing target is produced and is presented to the image acquisition assembly without use of a prismatic focusing aid wherein the anatomical target includes a fundus region of a human eye;

wherein the first field of view is wider than the second field of view, including a first field of view sufficiently wide to show at least an iris-scleral border; and wherein the optical apparatus is configured to be positionable by the user so that an alignment target appears to be located at or near the anatomical landmark when the optical apparatus is in a desired orientation for acquisition of an image of the fundus region.

* * * * *